United States Patent [19]

Kleemann et al.

[11] 4,326,056
[45] Apr. 20, 1982

[54] PROCESS FOR THE PRODUCTION OF 4-AMINO-6-TERT. BUTYL-3-MERCAPTO-1,2,4-TRIAZIN-5-ONE

[75] Inventors: Axel Kleemann, Hanau; Bernd Lehamnn, Friegericht; Herbert Klenk, Hanau, all of Fed. Rep. of Germany

[73] Assignee: Degussa Aktiengesellschaft, Frankfurt, Fed. Rep. of Germany

[21] Appl. No.: 266,147

[22] Filed: May 22, 1981

[30] Foreign Application Priority Data

May 29, 1980 [DE] Fed. Rep. of Germany ....... 3020370

[51] Int. Cl.³ .......................................... C07D 253/06
[52] U.S. Cl. .................................................... 544/182
[58] Field of Search ............................................ 544/182

[56] References Cited

U.S. PATENT DOCUMENTS

| | | | |
|---|---|---|---|
| 4,057,417 | 11/1977 | Dickore et al. | 544/182 |
| 4,058,526 | 11/1977 | Merz et al. | 544/182 |
| 4,071,684 | 1/1978 | Schuster et al. | 544/182 |
| 4,151,355 | 4/1979 | Merz | 544/182 |
| 4,175,188 | 11/1979 | Klenk et al. | 544/182 |

Primary Examiner—John M. Ford
Attorney, Agent, or Firm—Cushman, Darby & Cushman

[57] ABSTRACT

4-amino-6-tert.butyl-3-mercapto-1,2,4-triazin-5-one of the formula

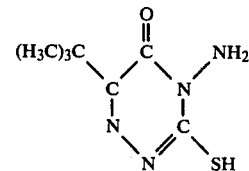

is produced by reacting pivaloyl cyanide and isobutylene in the presence of acetic acid and sulfuric acid, hydrolyzing the reaction mixture in the presence of water and reacting the trimethyl pyruvic acid formed with thiocarbohydrazide. The triazinone is an important intermediate product in the synthesis of the known herbicide 4-amino-6-tert.butyl-3-methylmercapto-1,2,4-triazin-5-one.

6 Claims, No Drawings

PROCESS FOR THE PRODUCTION OF 4-AMINO-6-TERT. BUTYL-3-MERCAPTO-1,2,4-TRIAZIN-5-ONE

BACKGROUND OF THE INVENTION

The invention is directed to a process for the production of 4-amino-6-tert.butyl-3-mercapto-1,2,4-triazin-5-one (I)

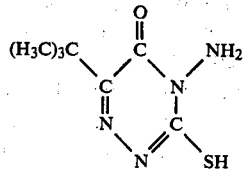

in which in a first reaction step pivaloyl cyanide (II)

is reacted with isobutylene in the presence of acetic acid and sulfuric acid and in a final reaction step the 4-amino-6-tert.butyl-3-mercapto-1,2,4-triazin-5-one (I) is formed by means of thiocarbohydrazide (III)

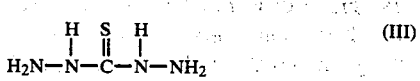

4-amino-6-tert.butyl-3-mercapto-1,2,4-triazin-5-one is an important intermediate product in the synthesis of the known herbicide 4-amino-6-tert.butyl-3-methylmercapto-1,2,4-triazin-5-one.

From German AS No. 2733180 (and related Klenk U.S. Pat. No. 4,175,188, the entire disclosure of which is hereby incorporated by reference and relied upon) there is already known a process for the production of 4-amino-6-tert.butyl-3-mercapto-1,2,4-triazin-5-one. In a first reaction step pivaloyl cyanide is reacted with isobutylene in the presence of acetic acid and 100% sulfuric acid and the trimethyl pyruvic acid tert.butylamide formed in this reaction is isolated. Subsequently the trimethyl pyruvic acid tert.butylamide is saponified by reacting with aqueous hydrochloric acid and the trimethyl pyruvic acid formed is isolated. In a final reaction step then the trimethyl pyruvic acid is subsequently condensed in aqueous-alcoholic solution with thiocarbohydrazide to form the 4-amino-6-tert.butyl-3-mercapto-1,2,4-triazin-5-one. In the industrial carrying out of the known process, however, the high accumulation of waste waters loaded with various types of inorganic and organic compounds is very disturbing. An economical working up of these waste waters is then hardly possible because of their complex composition. Besides the use of hydrochloric acid causes corrosion problems. Finally it is also not possible to at least partially recover the isobutylene employed.

SUMMARY OF THE INVENTION

The process of the invention is characterized by reacting pivaloyl cyanide (II) with isobutylene in the presence of 1.4 to 1.7 moles per mole of pivaloyl cyanide employed of sulfuric acid having a concentration between 93 and 100 weight percent, treating the reaction mixture obtained in this reaction with water and optionally more acetic acid in such amount that in each case it contains per mole of pivaloyl cyanide employed 50 to 200 grams of water and in all 150 to 850 grams of acetic acid with the proviso that the weight ratio of water to acetic acid is between 0.1 and 1.0, subsequently heating at boiling until by thin layer chromatography there is no longer detectable trimethyl pyruvic acid tert.butylamide,

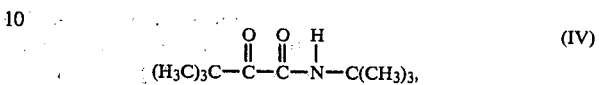

diluting the reaction mixture in a given case with so much water that the weight ratio of water to acetic acid is between 0.4 and 2.0 and precipitating the 4-amino-6-tert.butyl-3-mercapto-1,2,4-triazin-5-one (I) with an amount of thiocarbohydrazide (III) at least equivalent to the content of trimethyl pyruvic acid.

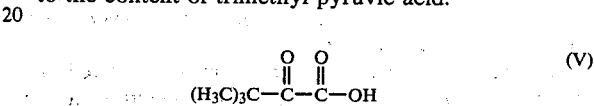

determined by cerimetric titration.

The process of the invention is carried out without isolation of intermediate product as a "one pot process" and consequently is industrially very simple. The accumulation of waste waters is considerably less than in the known process. Furthermore since only water and acetic acid are used as solvent the working up of the waste water is accomplished very much more easily. Besides at least a portion of the isobutylene employed can be recovered in a simple manner in reusable form. By suitable selection of the reaction conditions furthermore considerably higher yields can be produced based on the pivaloyl cyanide employed.

In regard to the possibility for recovery of the isobutylene employed and a high yield it is especially advantageous if the reaction mixture obtained in the reaction of pivaloyl cyanide with isobutylene is treated with water and optionally additional acetic acid in such an amount that it contains in each case per mole of pivaloyl cyanide employed, 100 to 200 grams of water and in all 250 to 450 grams of acetic acid with the proviso that the weight ratio of water to acetic acid is between 0.25 and 0.55.

The amount of acetic acid employed in the reaction of the pivaloyl cyanide with isobutylene is not decisive for the course of the reaction but there is suitably used per mole of pivaloyl cyanide employed 100 to 600 grams, preferably 150 to 250 grams, of acetic acid. The sulfuric acid is employed in an amount of 1.4 to 1.7 moles per mole of pivaloyl cyanide employed. The isobutylene also is suitably used in excess, for example in an amount of 1.7 to 2 moles per mole of pivaloyl cyanide employed. The temperature during the reaction can be varied within wide limits. Preferred are temperatures between −20° and +50° C., especially between 0° and +20° C.

The reaction mixture treated after ending the reaction with water and in a given case further acetic acid is subsequently heated until trimethyl pyruvic acid tert-butylamide is no longer detectable therein by thin layer chromatrography. The thin layer chromatographic examination takes place in the manner that a sample of reaction mixture is applied on a DC prepared plate (silica gel 60 F$_{254}$, layer thickness 0.25 mm; manufacturer: E. Merck, Art. No. 5714) and dried briefly. Then it is developed with ether as running means. After the evaporation of the solvent there is recognized any pyruvic acid tert.butylamide still present in UV light of wave length 254 nm as a spot with the R$_f$ value 0.67.

During the heating isobutylene split off escapes from the reaction mixture. The isobutylene can be caught in a cooling trap. It can be especially quickly and thoroughly removed from the reaction mixture by leading a weak stream of nitrogen through the reaction mixture.

Subsequently the reaction mixture in a given case is diluted with so much additional water that the weight ratio of water to acetic acid is between 0.4 and 2.0, preferably between 0.65 and 1.45, treated with at least the amount of thiocarbohydrazide equivalent to the content of trimethyl pyruvic acid determined by cerimetric titration and cooled to room temperature. Thereby the deisred 4-amino-6-tert.butyl-3-mercapto-1,2,4-triazine-5-one is precipitated in thin layer chromatographically pure form.

In order to suppress the formation of undesired and total yield reducing byproducts in this reaction step, it has proven advantageous to bring in the water employed before the addition of the thiocarbohydrazide in the form of an aqueous base, e.g. as aqueous ammonia or as soda lye (aqueous sodium hydroxide), in which case suitably the content of base should be equivalent to the amount of sulfuric acid still present in the reaction mixture. Naturally, however, there can also be used a slight excess of base.

This procedure at the same time favors the recovery of the acetic acid from the waste water remaining after the separation of the 4-amino-6-tert.butyl-3-mercapto-1,2,4-triazin-5-one since in the absence of free sulfuric acid there can also be employed successfully hydrolysis sensitive extraction agents such as ethyl acetate and without mentionable loss of extraction agents. Alternatively the acetic acid can also be recovered by distillation from the waste water. If ammonia is used to neutralize the sulfuric acid then the residue remaining can be worked up to ammonium sulfate, e.g. for the purpose of fertilizer.

Unless otherwise indicated, all parts and percentages are by weight.

The process can comprise, consist essentially of or consist of the recited steps with the stated materials.

The invention will be further explained through the following examples:

DETAILED DESCRIPTION

EXAMPLE 1

111 grams (1 mole) of pivaloyl cyanide were dissolved in 200 ml of glacial acetic acid and treated at 0° to +5° C. with 152 grams (1.5 moles) of 97% sulfuric acid. Within 2 hours there were led in 112.2 grams (2 moles) of isobutylene at 0° to +5° C. In connection with the one hour post reaction at 20° C. there were added at the same temperature 200 ml of glacial acetic acid and 108 grams of water. The mixture was heated at boiling in a very slow current of nitrogen for 4 hours, whereby 92 grams (82% of that employed) of isobutylene escaped and was caught in a cooling trap. The mixture was treated at 80° C. with 100 grams of water and subsequently with 92.4 grams (0.87 mole) of thiocarbohydrazide. It was stirred for a further 10 minutes at 95° to 100° C. and then cooled. By filtration there were isolated 162 grams of the triazinone (I) having a melting point of 208°-210° C. (81% of theory).

EXAMPLE 2

The procedure was the same as in Example 1 but before the addition of the thiocarbohydrazide instead of treating with 100 grams of water, there were employed 340 grams (2 moles) of 10% aqueous ammonia solution and subsequently there were used 93.4 grams (0.88 mole) of thiocarbohydrazide. There were isolated 174 grams (87% of theory) of the triazinone (I) having a melting point 209°-212° C. The acetic acid was extracted from the filtrate with ethyl acetate and recovered by distillation. By concentration and crystallization there were obtained from the residue of the extraction 194 grams (98% of theory) of ammonium sulfate.

EXAMPLE 3

111 grams (1 mole) of pivaloyl cyanide were dissolved in 200 ml of glacial acetic acid and treated at 0° to +5° C. with 152 grams (1.5 moles) of 97% sulfuric acid. Within 2 hours there were led in 112.2 grams (2 moles) of isobutylene at 0° to +5° C. In conjunction with the one hour post reaction there were added at 20° C. at the same temperature 200 ml of glacial acetic acid 198 grams of water. The mixture was heated at boiling for 12 hours in a very slow stream of nitrogen, whereby 97 grams (86% of that employed) of isobutylene escaped, which isobutylene was caught in a cooling trap.

The mixture was treated with 236 grams (2 moles) of a 14.4% aqueous ammonia solution and subsequently with 98 grams (0.92 mole) of thiocarbohydrazide. The mixture was stirred for a further 5 minutes at 100° C. and then cooled. By filtration there were isolated 182 grams (91% of theory) of triazinone (I) having a melting point of 209°-212° C.

EXAMPLES 4 to 10

In each case 111 grams (1 mole) of pivaloyl cyanide were dissolved in 210 grams of glacial acetic acid and treated at 0° to +5° C. with 152 grams (1.5 mole) of 97% sulfuric acid. Within 2 hours there were led in 112.2 grams (2 moles) of isobutylene at 0° to +5° C. In conjunction with the one hour post reaction at +20° C. there were added at the same temperature the amounts of acetic acid and water given in Table 1. The mixture was heated at boiling in a very slow stream of nitrogen until trimethyl pyruvic acid tert.butylamide no longer was detectable by thin layer chromatography. The isobutylene escaping was caught in a cooling trap and weighed. The content of trimethyl pyruvic acid in the reaction mixture was determined by cerimetric titration.

The mixture was treated with 236 grams (2 moles) of a 14.4% aqueous ammonia solution and subsequently with 102% of the amount of thiocarbohydrazide equivalent to the trimethyl pyruvic acid.

The mixture was heated to 100° C., stirred for about 5 to 10 minutes at this temperature and then allowed to cool. The triazinone (I) was isolated in thin layer chromatographically pure form by filtration.

TABLE I

| Example | Acetic Acid Addition before saponification (g) | Total Acid Acetic (g) | Water Addition (g) | Weight ratio water/total acetic Acid | Recovered isobutylene (% of Triazinone addition) | I % of Theory |
| --- | --- | --- | --- | --- | --- | --- |
| 4 | 0 | 210 | 63 | 0.30 | 30 | 62 |
| 5 | 0 | 210 | 108 | 0.51 | 69 | 83 |
| 6 | 0 | 210 | 198 | 0.94 | 48 | 67 |
| 7 | 210 | 420 | 63 | 0.15 | 16 | 72 |
| 8 | 210 | 420 | 108 | 0.26 | 82 | 87 |
| 9 | 210 | 420 | 198 | 0.47 | 86 | 91 |
| 10 | 630 | 840 | 108 | 0.13 | 17 | 86 |

Comparison Example 1

The procedure was as in Examples 4 to 6 except that after the reaction of the pivaloyl cyanide with the isobutylene there were added 378 grams of water. The weight ratio water/total acetic acid accordingly was 1.80:1. During 12 hours heating at reflux no isobutylene escaped from the reaction mixture. After this time the cerimetric titration gave a content of trimethyl pyruvic acid of only 5.85 grams (4.5 of theory).

Comparison Example 2

The procedure was as in Examples 7 to 9 except that after the reaction of the pivaloyl cyanide with the isobutylene there were added 378 grams of water. The weight ratio water/total acetic acid accordingly was 0.90:1. During 12 hours heating at reflux there only escaped about 5.6 grams (5% of that added) of isobutylene from the reaction mixture. After this time the cerimetric titration gave a content of trimethyl pyruvic acid of only 26 grams (20% of theory).

EXAMPLES 11 to 14

In each case 111 grams (1 mole) of pivaloyl cyanide were dissolved in 210 grams of glacial acetic acid and treated at 0° to +5° C. with 1.5 moles of sulfuric acid which had the water content given in Table 2. Within 2 hours there were led in 112.2 grams (2 moles) of isobutylene at 0° to +5° C. In conjunction with the one hour post reaction at +20° C. there were added at the same temperature 210 grams of glacial acetic acid and the amounts of water given in Table 2. The amounts of water were so chosen that the sum of the amount of water added and brought in through the sulfuric acid is equal.

The mixture was heated at boiling in a slow stream of nitrogen for 4½ hours.

The content of trimethyl pyruvic acid in the reaction mixture was determined by cerimetric titration.

The mixture was treated with 340 grams of 10% aqueous ammonia solution and subsequently with 102% of the amount of thiocarbohydrazide equivalent to the trimethyl pyruvic acid.

The mixture was heated to 95° C., stirred for 10 minutes at this temperature and then allowed to cool.

The triazinone (I) was isolated in thin layer chromatographically pure form by filtration.

TABLE 2

| Example | Water Content of the Sulfuric Acid in % | Water Content of the Sulfuric Acid in g | Water Addition in g | Table Water in g | Yield of Triazinone I % of Theory |
| --- | --- | --- | --- | --- | --- |
| 11 | 7 | 11.1 | 101.5 | 112.6 | 82.5 |
| 12 | 5 | 7.7 | 104.9 | 112.6 | 84.5 |
| 13 | 3 | 4.6 | 108 | 112.6 | 87 |
| 14 | 0 | 0 | 112.6 | 112.6 | 84 |

The entire disclosure of German priority application No. P 3020370.4-44 is hereby incorporated by reference.

What is claimed is:

1. In a process for the production of 4-amino-6-tert.butyl-3-mercapto-1,2,4-triazin-5-one (I)

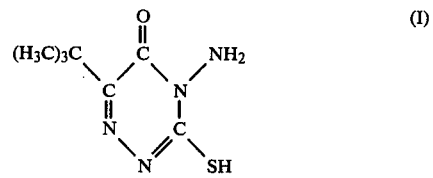

by reacting pivaloyl cyanide (II)

in a first reaction step with isobutylene in the presence of acetic acid and sulfuric acid and in a final reaction step forming the 4-amino-6-tert.butyl-3-mercapto-1,2,4-triazin-5-one (I) by means of thiocarbohydrazide (III)

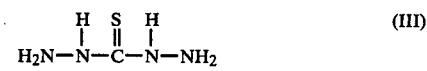

the improvement comprising reacting the pivaloyl cyanide (II) with isobutylene in the presence of 1.4 to 1.7 moles per mole of pivaloyl cyanide employed of sulfuric acid having a concentration between 93 and 100 weight percent, treating the reaction mixture obtained in this reaction with water and optionally more acetic acid in such amount that in each case it contains per mole of pivaloyl cyanide employed 50 to 220 grams of water and in all 150 to 850 grams of acetic acid with the proviso that the weight ratio of water to acetic acid is between 0.1 and 1.0:1, subsequently heating at boiling until by thin layer chromatography there is no longer detectable trimethyl pyruvic acid tert.butylamide

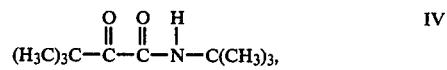

diluting the reaction mixture with enough water that the weight ratio of water to acetic acid is between 0.4 and 2.0 and precipitating the 4-amino-6-tert.butyl-3-mercapto-1,2,4-triazin-5-one (I) with an amount of thiocarbohydrazide (III) at least equivalent to the content of trimethyl pyruvic acid

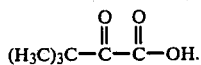 (V)

2. The process of claim 1 wherein in the treating of the reaction mixture obtained by the reaction of pivaloyl cyanide with isobutylene with water and optional acetic acid there is employed sufficient water and acetic acid that there is added per mole of pivaloyl cyanide 100 to 200 grams of water and in all 250 to 450 grams of acetic acid with the proviso that the weight ratio of water to acetic is between 0.25 and 0.55:1.

3. The process of claim 2 wherein the water added before the addition of the thiocarbohydrazide is added in the form of an aqueous base and the base is present in an amount at least equivalent to the amount of sulfuric acid still present in the reaction mixture.

4. The process of claim 1 wherein the water added before the addition of the thiocarbohydrazide is added in the form of an aqueous base and the base is present in an amount at least equivalent to the amount of sulfuric acid still present in the reaction mixture.

5. The process of claim 4 wherein the aqueous base is aqueous ammonia.

6. The process of claim 3 wherein the aqueous base is aqueous ammonia.